(12) United States Patent
Jang (10) Patent No.: US 10,473,483 B2
(45) Date of Patent: Nov. 12, 2019

(54) SMART SHOES, METHOD OF PROVIDING SENSOR INFORMATION TO SMART SHOES, SMART DEVICE AND METHOD OF PROVIDING GUIDANCE PROGRAM VIA SMART DEVICE

(71) Applicant: Electronics and Telecommunications Research Institute, Daejeon (KR)

(72) Inventor: Yong Won Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 831 days.

(21) Appl. No.: 14/588,560

(22) Filed: Jan. 2, 2015

(65) Prior Publication Data

US 2015/0182844 A1 Jul. 2, 2015

(30) Foreign Application Priority Data

Jan. 2, 2014 (KR) .................. 10-2014-0000084

(51) Int. Cl.
| | |
|---|---|
| *G01C 22/00* | (2006.01) |
| *G01G 19/50* | (2006.01) |
| *G01G 19/52* | (2006.01) |
| *A61B 5/103* | (2006.01) |
| *A61B 5/11* | (2006.01) |
| *A43B 3/00* | (2006.01) |

(52) U.S. Cl.
CPC .......... *G01C 22/006* (2013.01); *A43B 3/0005* (2013.01); *A61B 5/1036* (2013.01); *A61B 5/1112* (2013.01); *G01G 19/50* (2013.01); *G01G 19/52* (2013.01)

(58) Field of Classification Search
CPC ..... A61B 5/1036; A61B 5/1038; A61B 5/116; A61B 5/117; A61B 5/6807; A61B 5/6829; A61B 5/0022
USPC ................................ 600/587–595
See application file for complete search history.

(56) References Cited

U.S. PATENT DOCUMENTS

| | | | | |
|---|---|---|---|---|
| 5,925,001 A * | 7/1999 | Hoyt | .................... | A61B 5/1036 600/595 |
| 6,162,180 A * | 12/2000 | Miesel | .................. | A61B 5/083 600/481 |
| 6,836,744 B1 * | 12/2004 | Asphahani | ............... | A43D 1/02 377/24.2 |
| 7,878,055 B2 * | 2/2011 | Balzano | ............... | A61B 5/1036 340/573.1 |

(Continued)

FOREIGN PATENT DOCUMENTS

| | | |
|---|---|---|
| KR | 1020090049572 A | 5/2009 |
| KR | 1020100122617 A | 11/2010 |

(Continued)

*Primary Examiner* — Matthew Kremer
(74) *Attorney, Agent, or Firm* — William Park & Associates Ltd.

(57) ABSTRACT

Smart shoes including a sensor unit including at least one sensor of a pressure sensor to sense a pressure in the smart shoes, a temperature sensor to sense a temperature in the smart shoes, an acceleration sensor to sense a movement of the smart shoes and an altitude sensor to sense an altitude, a controller to collect sensor information output by the at least one sensor and process the collected sensor information according to a request from a user device, and a providing unit to provide the processed sensor information to the user device.

18 Claims, 9 Drawing Sheets

(56) References Cited

U.S. PATENT DOCUMENTS

| | | | |
|---|---|---|---|
| 8,212,158 B2 | 7/2012 | Wiest | |
| 8,917,167 B1* | 12/2014 | Selker | G06F 3/016 |
| | | | 340/407.1 |
| 2004/0210159 A1* | 10/2004 | Kibar | A61B 5/4803 |
| | | | 600/558 |
| 2005/0098640 A1* | 5/2005 | Ichishi | B60H 1/00742 |
| | | | 236/49.3 |
| 2009/0137933 A1* | 5/2009 | Lieberman | A61B 5/1036 |
| | | | 600/595 |
| 2009/0163834 A1* | 6/2009 | Wilssens | A61B 5/1036 |
| | | | 600/592 |
| 2014/0335490 A1* | 11/2014 | Baarman | A61B 5/002 |
| | | | 434/236 |

FOREIGN PATENT DOCUMENTS

| | | |
|---|---|---|
| KR | 1020120130306 A | 11/2012 |
| WO | 2009075446 A1 | 6/2009 |

* cited by examiner

SMART SHOES, METHOD OF PROVIDING SENSOR INFORMATION TO SMART SHOES, SMART DEVICE AND METHOD OF PROVIDING GUIDANCE PROGRAM VIA SMART DEVICE

CROSS-REFERENCE TO RELATED APPLICATION

This application claims the priority benefit of Korean Patent Application No. 10-2014-0000084, filed on Jan. 2, 2014, in the Korean Intellectual Property Office, the disclosure of which is incorporated herein by reference.

BACKGROUND

1. Field of the Invention

The following description relates to smart shoes, an operating method of the smart shoes, a user device and an operating method of the user device, and more particularly, to smart shoes and a user device for healthcare that may measure a weight and provide exercise guidance.

2. Description of the Related Art

Conventionally, information on the center of gravity of a user and a pressure level applied to shoes are determined using shoes including a sensor. Here, the determined information includes data related to a manner in which a user walks, such as a walking posture, a number of strides, and a walking speed. The information may be applicable to various areas, for example, weight management and healthcare of the user.

However, the determined information may not consider basic information, such as a weight of clothes worn by the user and a foot shape of the user. Thus, the determined information does not include accurate information about the weight of the user, the center of gravity, and an amount of pressure applied to the soles of the user feet while walking.

Although various shoes have been recently proposed to resolve conventional problems, such shoes include separate devices, diminish user convenience, or impede measurement of accurate information due to improper walking habits of the user.

Accordingly, a shoe-type device which extracts accurate information about the body of the user and is applicable to weight management and healthcare for the user based on the extracted information is needed.

SUMMARY

An aspect of the present invention provides smart shoes, a sensor information providing method of the smart shoes, a smart device and a guidance program providing method of the smart device which measure weight of the user considering an ambient temperature and a weight of clothes worn by the user when measuring the weight of the user using the smart shoes, thereby improving accuracy in measuring the weight of the user and thus, providing reliable weight measurement.

Another aspect of the present invention also provides smart shoes, method of providing sensor information to the smart shoes and a smart device, and a method of providing a guidance program to the via a smart device enabling convenient weight and health management of the user through the smart device based on sensor information collected by a sensor included in or detachable from the smart shoes, thereby providing advanced concept health equipment and services.

Still another aspect of the present invention provides smart shoes, method of providing sensor information to the smart shoes and a smart device, and method of providing a guidance program via the smart device which shares a result measured by a guidance program among different users through a social network, thereby inducing user interest in the guidance program, and checking physical conditions of current users.

According to an aspect of the present invention, there is provided smart shoes including a collection unit to collect sensor information based on a user movement using a sensor detachable from the shoes and a providing unit to provide the collected sensor information to a user device according to a request from the user device, wherein the sensor includes at least one of a pressure sensor to sense a pressure in the smart shoes, a temperature sensor to sense a temperature in the smart shoes, an acceleration sensor to sense a movement of the smart shoes, and an altitude sensor to sense an altitude.

According to another aspect of the present invention, there is provided a user device including a reception unit to receive, from the smart shoes, sensor information output by at least one of a pressure sensor, a temperature sensor, an acceleration sensor and an altitude sensor, an analysis unit to analyze the sensor information based on a request for weight management and healthcare for a user, and a providing unit to provide a guidance program according to the request using the analyzed sensor information, wherein the providing unit provides feedback on the sensor information output by the sensor corresponding to the user moving according to the provided guidance program.

According to an aspect of the present invention, there is provided a method of providing sensor information to smart shoes, the method including collecting sensor information based on a user movement using a sensor included in or detachable from the smart shoes and providing the collected sensor information to a user device according to a request from the user device, wherein the sensor includes at least one of a pressure sensor to sense a pressure in the smart shoes, a temperature sensor to sense a temperature in the smart shoes, an acceleration sensor to sense a movement of the smart shoes, and an altitude sensor to sense an altitude.

According to an aspect of the present invention, there is provided method of providing a guidance program via a user device, the method including receiving, from the smart shoes, sensor information output by at least one of a pressure sensor, a temperature sensor, an acceleration sensor and an altitude sensor, analyzing the sensor information based on a request for weight management and healthcare for a user, and providing a guidance program according to the request using the analyzed sensor information, wherein the providing provides feedback on the sensor information output by the sensor corresponding to the user moving according to the provided guidance program.

As described above, the smart shoes, the method of providing sensor information to the smart shoes, the smart device, and the method of providing the guidance program via the smart device measure a weight of the user considering an ambient temperature and a weight of clothes worn by the user when measuring the weight of the user using the smart shoes, thereby improving accuracy in measuring the weight of the user and thus, providing reliable weight measurement.

A method of providing sensor information to the smart shoes, a smart device, and a method of providing a guidance program via the smart device to enable a user to conveniently manage weight and health through the smart device based on sensor information collected by an embedded sensor included in the smart shoes or module-type sensor detachable from the smart shoes, thereby providing advanced concept health equipment and services.

A method of providing sensor information to the smart shoes, a smart device, and a method of providing a guidance program via the smart device to share a result measured by the guidance program among different users through a social network, thereby inducing user interest in the guidance program and checking physical conditions of current users.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Hereinafter, exemplary embodiments are described in detail with reference to the accompanying drawings.

Figure 1:
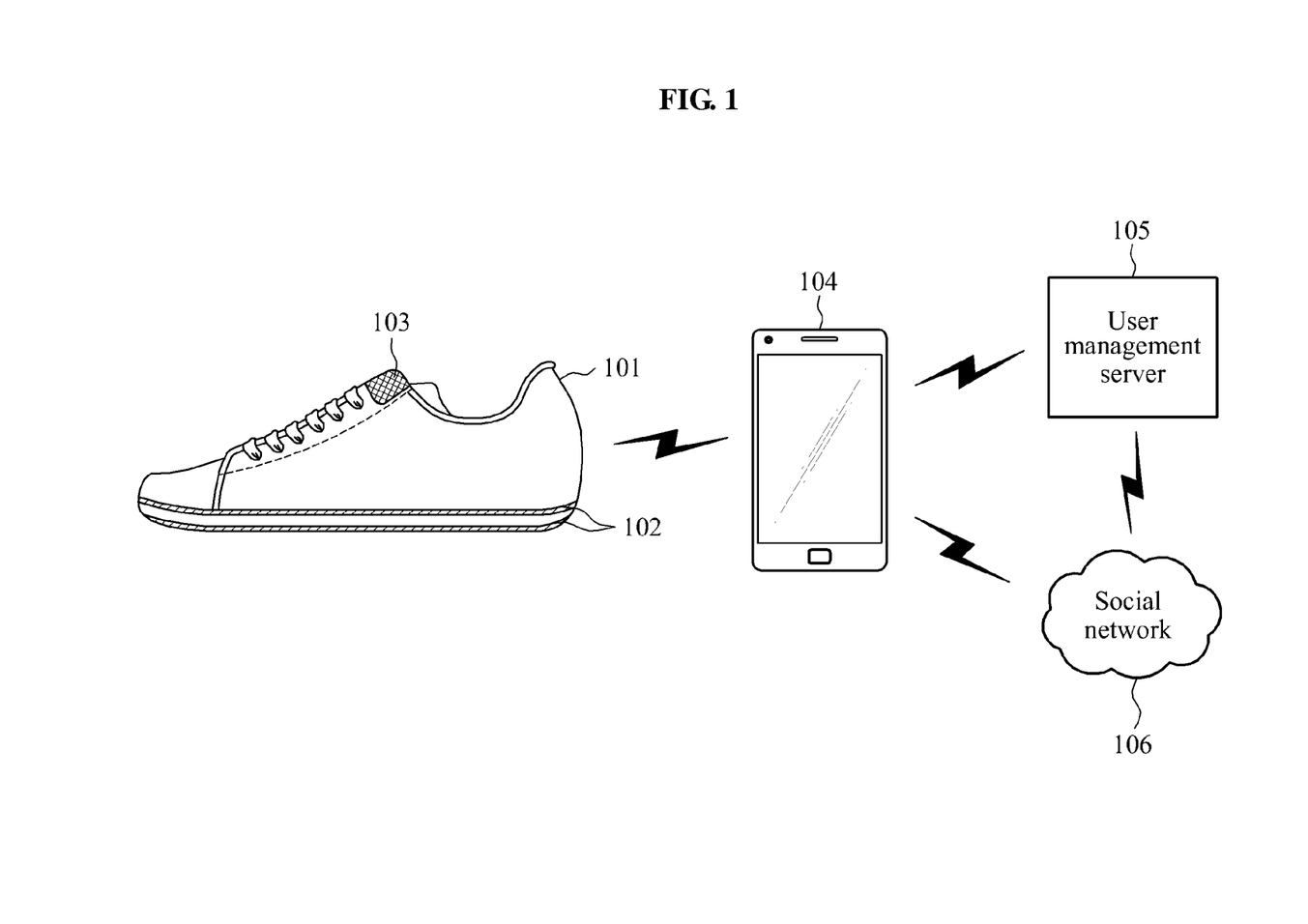
FIG. 1 illustrates an overall configuration of smart shoes according to an embodiment.

FIG. 1 illustrates an overall configuration of smart shoes according to an embodiment.

Referring to FIG. 1, the smart shoes 101 may include a sensor for measuring a weight of a user and providing exercise guidance. The sensor may include at least one of pressure sensors 102 and 103 to sense pressure in the smart shoes, a temperature sensor to sense temperature in the smart shoes, an acceleration sensor 102 to sense a movement of the smart shoes, and altitude sensors 102 and 103 to sense an altitude. Here, the same types of sensors may be disposed at different positions based on information to be sensed.

The sensor may be secured to the smart shoes 101 or detachable from the smart shoes 101. For example, the sensor may be attached as a shoe accessory to an insole, a shoelace, a buckle or the like to be detachable from the shoes. The sensor is detachable and thus, may be attached to any position. That is, the sensor may be embedded in the smart shoes 101 in an integral form or be provided in a detachable module type.

A pressure sensor 102 may be attached to an insole or an outsole of the smart shoes to sense pressure due to the weight of the user. Here, when the pressure sensor 102 is attached to the insole, the insole may be replaced with an insole of another shoe with the same size. That is, the pressure sensor-attached insole may be replaceable with an insole of shoes to be worn by the user, and accordingly the pressure sensor of the insole may sense a pressure by the weight of the user.

A pressure sensor 103 may be attached to a tongue of the smart shoes or mounted on the smart shoes as an accessory to sense pressure due to a user movement.

The temperature sensor 103 may be attached to an outside of the tongue of the smart shoes or mounted on the smart shoes as an accessory to measure external temperature when the weight of the user is measured. The temperature sensor 103 may measure an ambient temperature to estimate weather conditions corresponding to the measured ambient temperature. For example, the temperature sensor 103 may estimate spring, summer, fall, and winter weather conditions based on the measured ambient temperature, which will be described with reference to FIG. 2.

The acceleration sensor 102 may be attached to the insole or the outsole of the smart shoes to sense a movement due to movement of a user. That is, the acceleration sensor 102 may detect an acceleration based on the movement of a user. The detected acceleration may be used for analysis of user movements, such as workrate calculating algorithms, calorie consumption, movement patterns, and postures, through a guidance program.

The altitude sensors 102 and 103 may be attached to the insole, the outsole or the tongue of the smart shoes or be mounted on the smart shoes as an accessory to measure an altitude of a location of the user. For example, when the user putting on the smart shoes 101 participates in activities involving altitude changes, for example, mountain climbing or skiing, the altitude sensors 102 and 103 may measure an altitude based on altitude changes.

The smart shoes 101 may be associated with a user device 104. The smart shoes 101 may provide sensor information sensed by the sensor to the user device 104 so as to measure the weight of the user and provide exercise guidance.

The user device 104 may include commonly used terminals, such as a separate device or smart device carried by the user. The user device 104 may provide information to the user through a program capable of measuring the weight of the user and guiding exercises.

The user device 104 may receive sensor information output by at least one of the pressure sensors, the temperature sensor, the acceleration sensor and the altitude sensors. The user device 104 may analyze the sensor information for weight management and healthcare for the user based on a request from the user. The user device 104 may provide a guidance program to the user based on the request using the analyzed sensor information. The user device 104 may provide a guidance program for weight management and healthcare for the user in association with a user management server 105. The user device 104 may feed information relating to exercises specific to the user back to the user using the guidance program.

Further, the user device 104 may share results relating to user exercising among diverse users through a social network. That is, the user device 104 uploads an exercising result and health conditions to the social network, thereby sharing results relating to user exercises among social network users.

Figure 2:
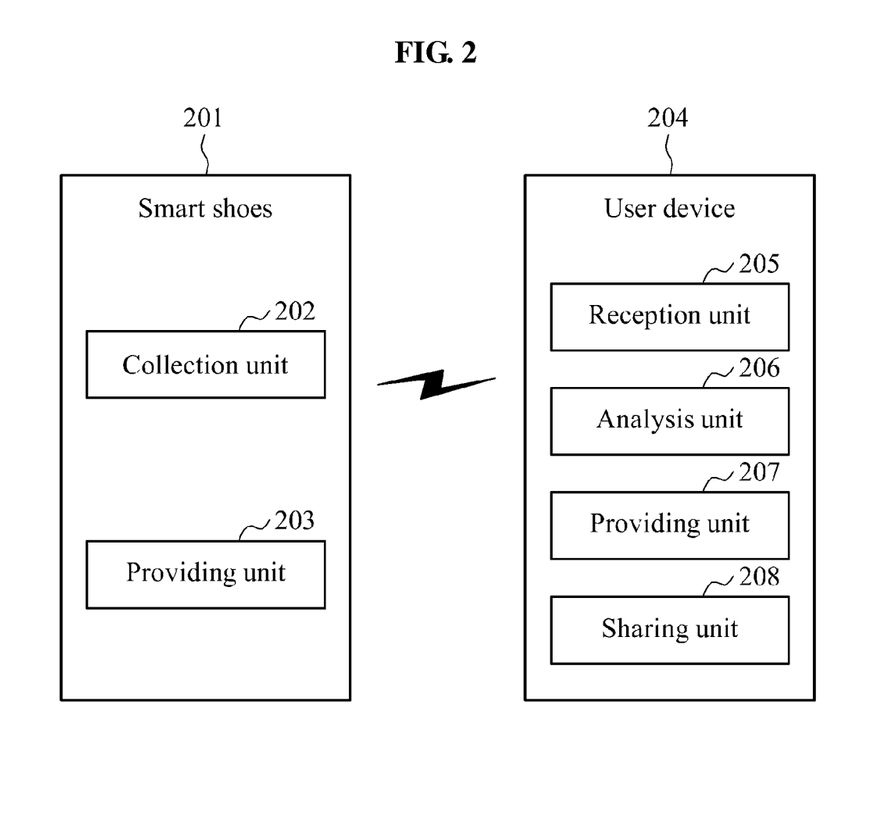
FIG. 2 is a block diagram illustrating smart shoes and a user device according to an embodiment.

FIG. 2 is a block diagram illustrating smart shoes 201 and a user device 204 according to an embodiment.

Referring to FIG. 2, the smart shoes 201 may include a collection unit 202 and a providing unit 203. In detail, the collection unit 202 may collect sensor information based on a user movement using a sensor included in or detachable from the shoes. The collection unit 202 may include at least one sensor among a pressure sensor to sense pressure in the smart shoes 201, a temperature sensor to sense temperature in the smart shoes 201, an acceleration sensor to sense a shoe movement, and an altitude sensor to sense an altitude.

The pressure sensor may be disposed on an insole, an inside bottom surface of the shoes or an instep contact surface coming in contact with an instep of a user foot so as to measure the weight of the user based on a distribution of foot joints of the user. That is, pressure sensors may be disposed for both feet in all areas to measure the weight in accordance with the foot joints of the user. The pressure sensors may include a customized type and a general type considering individual differences in distribution of foot joints. For example, the pressure sensors may include a customized type for distribution of foot joints of flat feet and a general type for feet of ordinary users to measure an individual weight. Here, the customized type may be modified for different distributions of foot joints.

When coming into contact with soles of the user foot, the insole or inside bottom surface of the shoes may measure a pressure applied to the insole or inside bottom surface of the shoes through pressure sensors embedded in or detachable from the insole or inside bottom surface of the shoes. The insole or inside bottom surface of the shoes may identify a distribution of foot joints for the user based on the measured pressure and adjust a sensor density of the pressure sensors according to the identified distribution of the foot joints.

For instance, when coming in contact with the soles of the user foot as the user puts on the smart shoes, the insole or inside bottom surface of the shoes may adjust the sensor density of the pressure sensors based on the distribution of the foot joints. Here, the insole or inside bottom surface may operate once when the user first puts on the smart shoes, or repeatedly operate whenever the user wears the smart shoes.

A volume of the insole or inside bottom surface of the shoes may be adjusted in accordance with a region in which the foot joints of the user are not distributed. For example, when coming into contact with the sole of the user foot, the insole or inside bottom surface of the shoes may identify the distribution of the foot joints based on a pressure applied to the insole and inside bottom surface of the shoes and adjust the volume of the insole or inside bottom surface of the shoes to correspond to an arch shape of the sole of the user foot. That is, a shape of the insole and inside bottom surface of the shoes may be adjusted to correspond to the shape of the user sole.

When high pressure is applied to the pressure sensors as the user walks, the pressure sensors may adjust sensor density of pressure sensors to which the high pressure is applied to measure a load of a corresponding area. For example, the pressure sensors may reduce sensor density of pressure sensors disposed in a high-pressure area, for instance, heels of the feet, to measure the weight of the user. That is, when a high pressure is applied, the pressure may be accurately measured with a low signal, and accordingly sensor density of pressure sensors to which the high pressure is applied may be reduced in measuring the weight of the user.

The providing unit 203 may provide the user device 204 with sensor information collected according to a request for use from the user device 204. Here, the providing unit 203 may provide different types of sensor information to the user device based on a current status of the user and an operation of the user device. That is, when a change in altitude occurs at a current location of the user, the providing unit 203 may provide sensor information sensed by the altitude sensor to the user device. When altitude is not changed, the providing unit 203 may not provide the sensor information by the altitude sensor to the user device.

That is, the providing unit 203 may provide the user device with the sensor information collected according to the use request from the user device or sensor information by a sensor based on changes in external environment.

The user device 204 may include a reception unit 205, an analysis unit 206, a providing unit 207 and a sharing unit 208. The reception unit 205 may receive, from the smart shoes, sensor information output by at least one sensor among a pressure sensor, a temperature sensor, an acceleration sensor, and an altitude sensor.

The analysis unit 206 may analyze the sensor information based on a request for weight management and healthcare for the user. The sensor information may be sensed by at least one of the acceleration sensor, the pressure sensor, the temperature sensor, and the altitude sensor.

The analysis unit 206 may analyze the weight of the user based on a weight change of the user in measuring weight. Here, the weight of the user may change based on a volume of clothes worn by the user. Here, the volume and weight of clothes the user wears may change depending on current weather conditions. That is, clothes suitable for −20° C. and 30° C. temperatures differ in terms of volume and weight. Thus, the analysis unit 206 may analyze the weight of the user considering the volume of clothes worn by the user.

For instance, the analysis unit 206 may first measure an ambient temperature of the user wearing clothes suitable for current weather conditions. The analysis unit 206 may measure the ambient temperature of the user at regular intervals. The analysis unit 206 may compare the first measured ambient temperature of the user with the ambient temperatures of the user measured at regular intervals. The analysis unit 206 may analyze the weight of the user more accurately using a temperature difference resulting from a comparison. For example, when there is a change in the weight of the user measured for a predetermined period, the analysis unit 206 may recognize that the change of the weight is due to the volume of clothes worn by the user in view of the ambient temperature. That is, the analysis unit 206 may analyze that an error in the weight of the user occurs by the volume of the clothes worn by the user depending on weather conditions.

The temperature of the user increases with a greater volume of clothes worn by the user and decreases with a smaller volume of clothes worn by the user. Thus, the analysis unit 206 may determine that a large temperature difference means a great volume of clothes, and analyze a load excluding a weight based on the volume of the clothes as the weight of the user. Here, the weight based on the volume of the clothes may be measured by a weight estimating algorithm.

The analysis unit 206 may analyze a distribution of foot pressure according to the weight of the user on the basis of sensor information output by the pressure sensors. The analysis unit 206 may analyze a physical balance for healthcare of the user based on the distribution of foot pressure according to the weight of the user. The pressure sensors may be disposed across the soles on either or both of the feet so as to measure a load of the user. The analysis unit 206 may analyze a drastic difference in weight measured between both feet and distribution of the weight. The analysis unit 206 may determine based on an analysis result whether the user carries a bag on the back or over one shoulder.

The analysis unit 206 may identify a change in the walking manner of the user based on the analyzed distribution of foot pressure. The user device 204 may lead the user to walk in a proper manner through gait analysis based on the identified change in the walking manner. For example, when the user walks for a long time, carrying a bag over one shoulder, the user device 204 may correct a walking manner of the user through gait analysis so as to prevent a disturbance in a physical balance of the user.

The analysis unit 206 may analyze at least one of an activity pattern and calorie consumption of a user movement. For user healthcare, the analysis unit 206 may analyze at least one of the activity pattern and calorie consumption of the user movement on the basis of at least one of an exercise type, an exercising style, an exercise duration, and an exercise intensity according to the user movement using sensor information.

The user device 204 may use the analyzed activity pattern and calorie consumption for weight management and healthcare for the user, for exhibiting individual exercise effects and for motivational purposes.

The providing unit 207 may provide a guidance program according to the request using the analyzed sensor information. The guidance program may include a guidance application to guide the user through exercises, and a management application for recoding and managing the sensor information received through the smart shoes 201.

The guidance application may be an application providing assistance to the user wearing the smart shoes 201 to properly follow exercise motions. The guidance application may compare a motion preset in the guidance application with a motion of an analysis result analyzed through sensor information transmitted in real time via the smart shoes 201. The user device 204 may provide feedback on whether the user properly follows the exercise motions based on a result of the guidance application comparing the exercise motions.

The management application may record and manage the sensor information received via the smart shoes 201 on a daily, monthly, or quarterly basis.

Here, the guidance program including the guidance application and the management application may be downloaded through a user management server and a cloud service commonly available via an application server. For example, the guidance program may be downloaded through a server commonly available using wireless networks including 3G, 4G and WiFi.

The sharing unit 208 may share a result relating to user exercising among diverse users through a social network. That is, the sharing unit 208 may upload an exercising result and health conditions of the user to the social network, thereby sharing results relating to user exercising among social network users.

Figure 3:
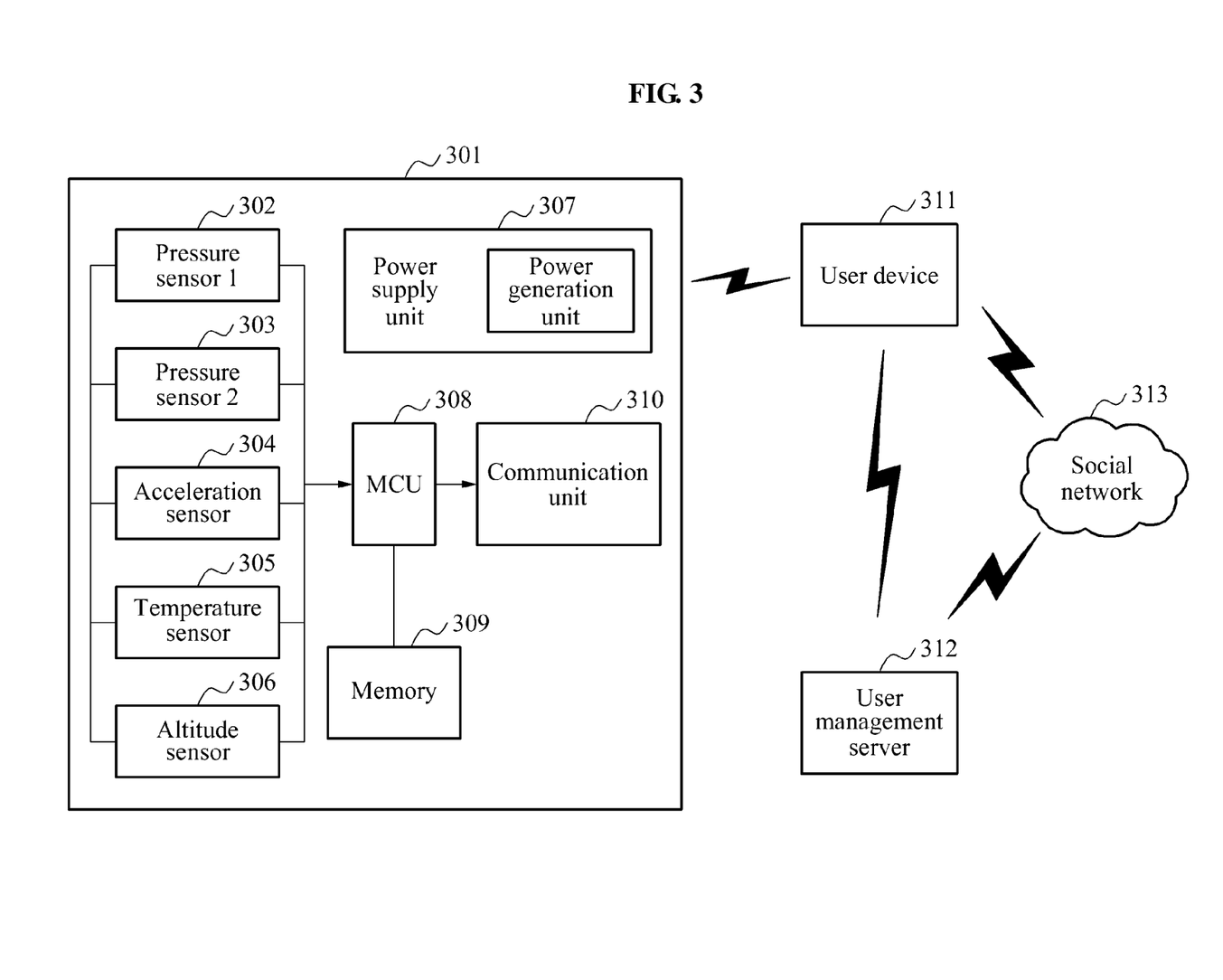
FIG. 3 is a block diagram illustrating a detailed configuration of smart shoes according to an embodiment.

FIG. 3 is a block diagram illustrating a detailed configuration of smart shoes 301 according to an embodiment.

Referring to FIG. 3, the smart shoes 301 may include a pressure sensor 1 302, a pressure sensor 2 303, an acceleration sensor 304, a temperature sensor 305, an altitude sensor 306, a power supply unit 307, an MCU 308, a memory 309, and a communication unit 310.

The power supply unit 307 provides power to the smart shoes 301 and may have an energy harvesting function using current/voltage generated by movements. Here, the power supply unit 307 may perform the energy harvesting function through a power generation unit included therein.

The MCU 308 may collect sensor information output by at least one of the pressure sensor 1 302, the pressure sensor 2 303, the acceleration sensor 304, the temperature sensor 305, and the altitude sensor 306 and process the collected sensor information according to a request from the user device 311. The MCU 308 may store the collected sensor information in association with the memory 309.

The communication unit 310 may provide the processed sensor information to the user device 311.

The user device 311 may analyze the sensor information received from the smart shoes 301 according to a request and output an analysis result of the sensor information. The user device 311 may provide feedback on a motion relating to user exercising based on the analysis result in association with a user management server 312. Here, the user device 311 may provide the feedback through a program included in the user device 311. The program may include a guidance application and a management application.

The guidance application is an application which aids the user wearing the smart shoes 201 in properly following an exercise, providing various types of aid in view of an age, gender, situation, and physique of a user.

The management application is to record and manage the sensor information received through the smart shoes 301 and may provide a weight/exercise information storing and transmitting function, a weight/exercise viewer function, a user information setting function, a guidance application loading function, a guidance application use history and result recording function, or the like.

The user management server 312 may upload a use result of the smart shoes 301 with respect to the analysis result by the user device 311. The user management server 312 may regularly or irregularly provide the use result to an expert, and the expert may provide feedback on the use result to the user.

In one exemplary embodiment, the user may be provided with guidance information on weight management and exercise management via a guidance program through the user management server 312. The user may do exercise according to the guidance program. The smart shoes 312 may collect sensor information by a sensor on a moving user based on the guidance information and transmit the collected sensor information to the user device 311. The user device 311 may analyze the transmitted sensor information and transmit an analysis result to the user management server 312 according to a use request. The expert may monitor the analysis result transmitted to the user management server 312 and provide feedback on a result of a motion relating to the exercise back to the user.

The user device may upload a feedback result via the guidance program from the expert or a quest result based on an exercise schedule to a social network to share among diverse users.

Figure 4:
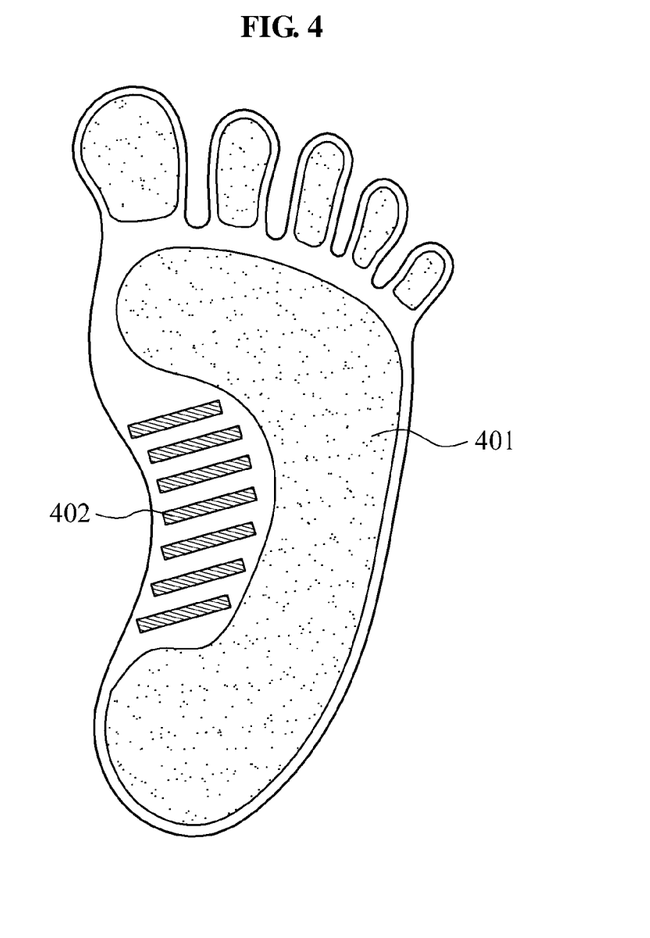
FIG. 4 illustrates a process of analyzing distribution of foot pressure of a user according to an embodiment.

FIG. 4 illustrates a process of analyzing distribution of foot pressure of a user according to an embodiment.

Referring to FIG. 4, pressure sensors 401 and 402 may be disposed by two methods depending on a distribution of foot joints. In a first method, initial foot pressure of the user may be analyzed using a separate foot pressure analyzer and the pressure sensors 401 and 402 may be disposed on soles of the user based on the analyzed initial foot pressure. In a second method, the pressure sensors 401 and 402 are disposed at regular intervals across the soles based on the distribution of the foot joints of the user, adjusting sensor density of the pressure sensors 401 and 402 in an area where foot pressure is absent. For example, sensor density of pressure sensors 401 disposed in an area where foot pressure is distributed may be different from sense density of pressure sensors 402 disposed in an area where no foot pressure is distributed.

The smart device may analyze the distribution of the foot pressure of the user using a foot pressure distribution analysis algorithm. The foot pressure distribution analysis algorithm may receive an input of initial weight information on the user from the user to measure foot pressure distribution of the user. The foot pressure distribution analysis algorithm may measure new foot pressure distribution of the user in a stationary state detected by an acceleration sensor included in smart shoes. The foot pressure distribution analysis algorithm may compare the foot pressure distribution measured based on the input with the new foot pressure distribution. The foot pressure distribution analysis algorithm may present a comparison result including information on whether levels of the foot pressure distribution measured based on the input and the new foot pressure distribution are high or low.

The foot pressure distribution analysis algorithm may identify a change in the walking manner of the user based on the comparison result. That is, the foot pressure distribution analysis algorithm may identify changes in the walking manner when the user carries a back on a left shoulder, a right shoulder, and both shoulders. When the center of gravity of the user leans to one side, the user may have a spinal abnormality, for example, scoliosis, caused by postural imbalance. Thus, changes in the walking manner may be identified in advance to prevent such spinal abnormalities.

The user device may estimate a mental condition of the user according to a walking posture and walking type of the user by identifying the change in the walking manner through the foot pressure distribution analysis algorithm. The user device may provide the user with various contents suited to a current state of the user depending on an estimation result. Here, the contents may present exercises or suggest a rest period in view of the estimated walking posture and mental condition of the user. Due to the various contents associated with the current state provided from the user device, the user may receive effective help in preventing a disease and promoting mental health of the user.

Figure 5:
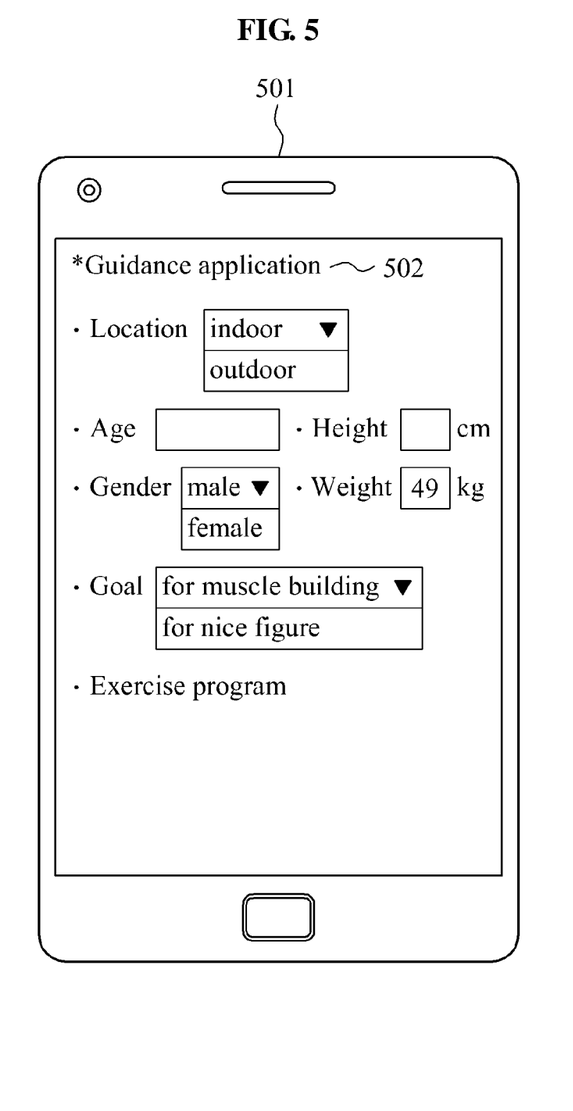
FIG. 5 illustrates a guidance application according to an embodiment.

FIG. 5 illustrates a guidance application according to an embodiment.

Referring to FIG. 5, the guidance application 502 may provide a personal workout trainer function for the user in association with sensor information received from smart shoes. In detail, the guidance application 502 may provide various exercise programs based on a use request and a user condition. Here, the guidance application 502 may provide guidance movements for the user using the sensor information received from the smart shoes so that the user performs an exercise according to instructions of an exercise program. That is, the guidance application 502 may reset the program to detect user movements using sensor information so as to adjust a movement speed or to correct improper movements. For instance, the guidance application 502 may reset the program to check movements not performed by the user to ensure that the user performs the checked movements.

Further, the guidance application 502 may include diverse programs adapted for purposes, such as indoor exercise programs for a fitness center or the like, outdoor exercise programs for a playground or the like, programs by age group, programs by gender, weight training programs, or programs for improving a figure.

The guidance application 502 may provide feedback on exercise pacing, music selection, or the like based on an age, gender, physique, situation group of the user considering a current temperature, an exercise type, intensity, time, and conditions.

Figure 6:
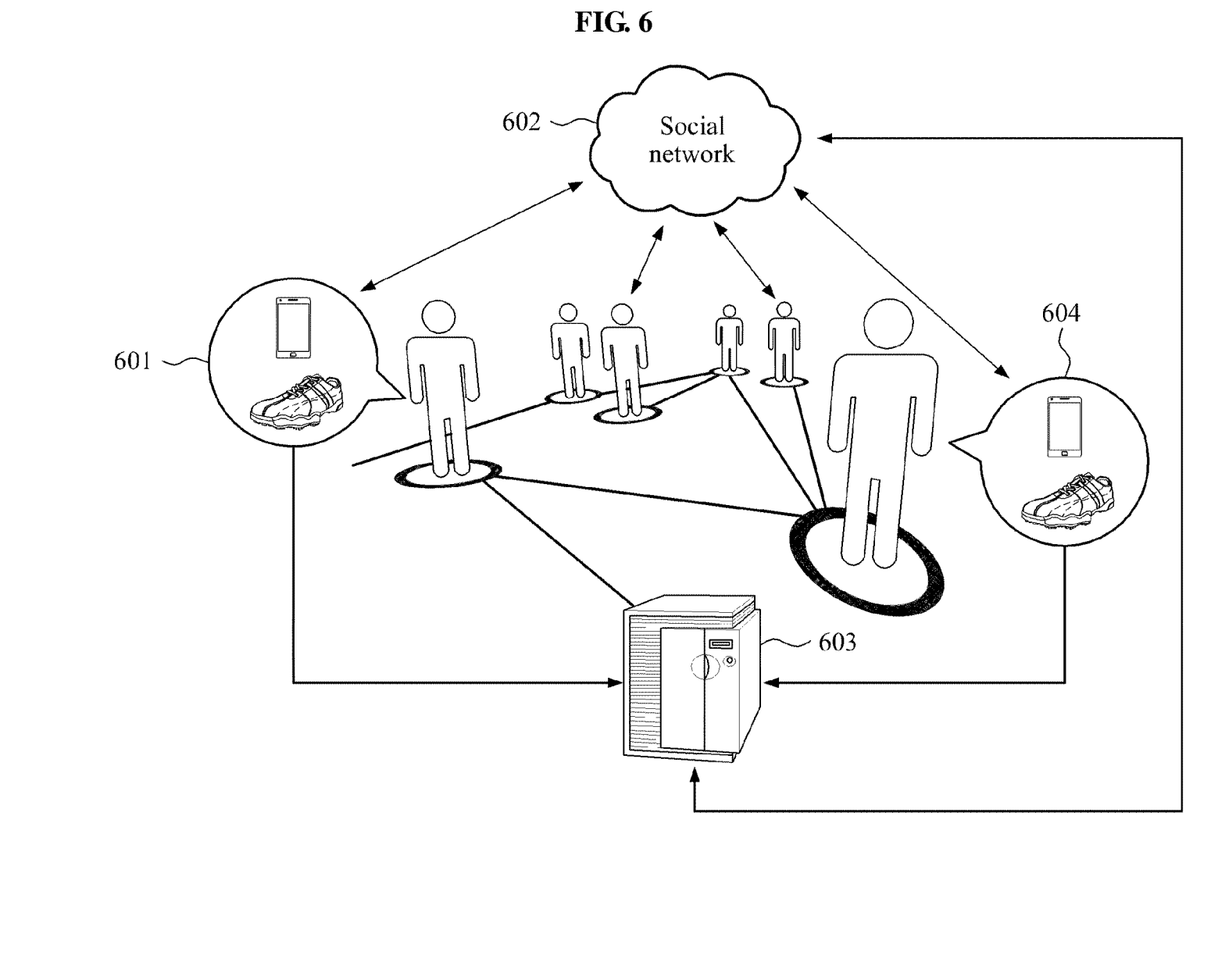
FIG. 6 illustrates a user device in association with a social network according to an embodiment.

FIG. 6 illustrates a user device in association with a social network according to an embodiment.

Referring to FIG. 6, user devices 601 and 604 may share a result measured through a guidance program among diverse users using a social network 602. That is, the user devices 601 and 604 may upload the measured result to the social network 602. The uploaded result may be stored by user in a network server 603.

Here, the user devices 601 and 604 may upload a measured result of a user to at least one of various groups, such as a chatting group and a club. The uploaded result may be entirely or partially made public based on access information of different users.

For example, the user devices 601 and 604 may upload a measured result relating to a user exercising to a chat room of a mountaineering club to which the user belongs. Here, the uploaded result may include a mountain name that the user is currently climbing, a height or an altitude at which the user is currently located, and current physical conditions of the user. Other users belonging to the mountaineering club may identify health information on the user who uploaded the result.

The network server 603 may collect uploaded results by user and provide ranking information on the users belonging to the club. That is, the network server 603 may identify characteristics of the club and select various ranking subjects, for example, a user who climbs to a highest point and a user with a greatest physical strength, based on the uploaded results to the mountaineering club. The network server 602 may rank the users according to a selected subject and provide ranking information to the users of the club.

The user devices 601 and 604 may share information relating to exercise among users through the social network 602, thereby suggesting not only exercise for individuals but also an exercise program in a similar form to a group activity. That is, the user devices 601 and 604 may provide not only an exercise history of individuals but also an exercise history of a plurality of users through the social network, thereby inducing user interest in an exercise regimen.

Figure 7:
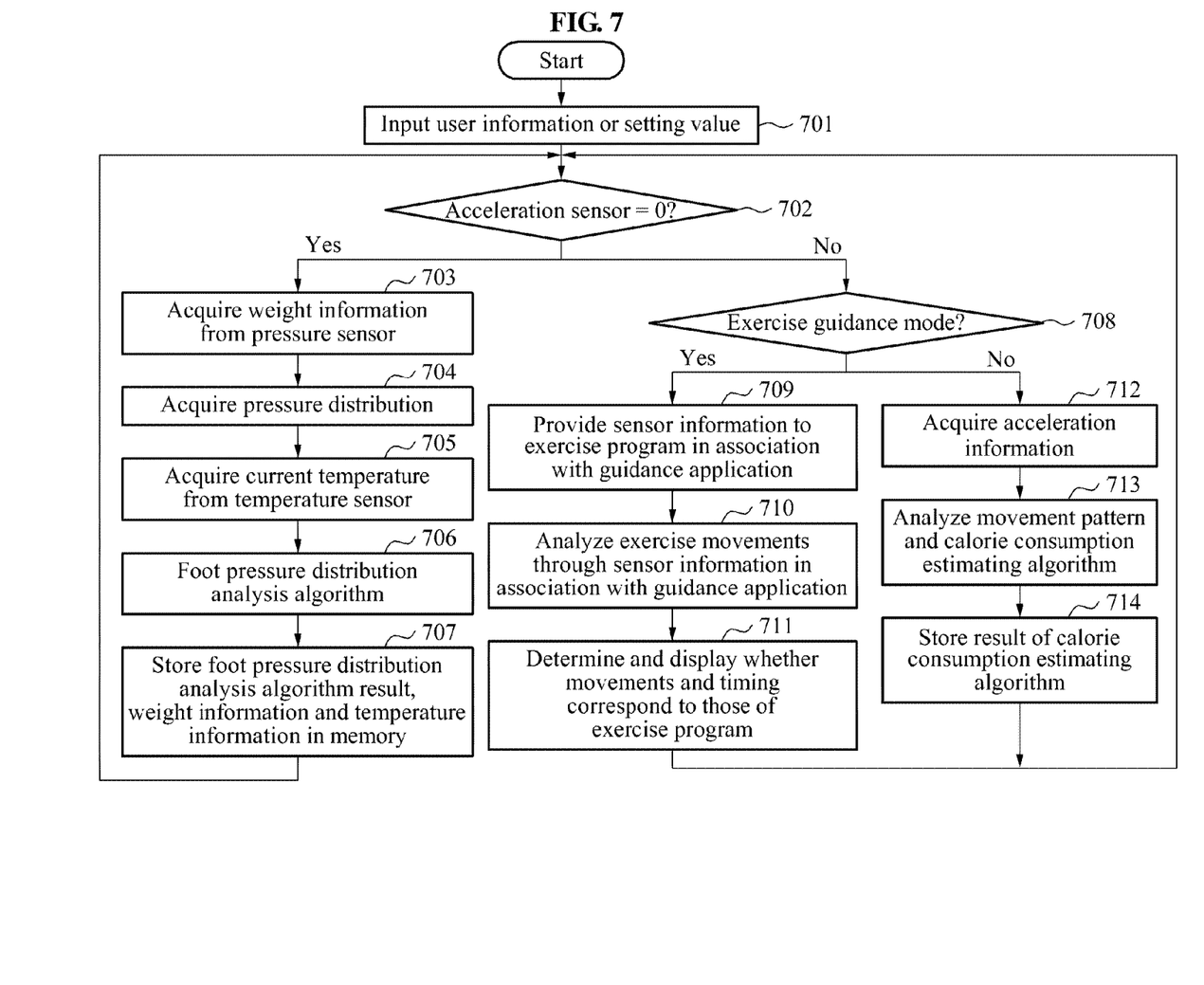
FIG. 7 is a flowchart illustrating a user device according to an embodiment.

FIG. 7 is a flowchart illustrating a user device according to an embodiment.

In operation 701, the user device may receive an input of user information or setting value from a user. Here, the user information or setting value may include information on an initial weight of the user.

In operation 702, the user device may determine whether there is a user movement using sensor information by an acceleration sensor received from smart shoes.

When an acceleration is not detected by the acceleration sensor YES in operation 702, the user device may acquire information on weight of the user from a pressure sensor in operation 703 and acquire pressure distribution by the pressure sensor corresponding to the information on the weight of the user in operation 704.

In operation 705, the user device may acquire current temperature information from a temperature sensor so as to accurately determine the weight of the user and estimate weather conditions based on the temperature information. The user device may measure a weight of clothes worn by the user through a weight estimating algorithm for measuring the weight of the clothes based on the estimated weather conditions, and correct the weight of the user based on the weight of the clothes.

In operation 706, the user device may analyze a foot pressure distribution of the user through a foot pressure distribution analysis algorithm based on the sensor information sensed by the pressure sensor. The user device may compare the information on the initial weight of the user and newly measured foot pressure distribution to identify a state of the foot pressure distribution of the user.

In operation 707, the user device may store a result of the foot pressure distribution analysis algorithm, the information on the weight of the user and the temperature information in a memory. Here, storing the information in the memory may refer to transmitting the information to and storing the information in a user management server.

When an acceleration is detected by the acceleration sensor NO in operation 702, the user device may verify whether the user device is in an exercise guidance mode in operation 708. When the user device is in the exercise guidance mode YES in operation 708, the user device may provide sensor information received from smart shoes to a guidance application or the user management server in association with the guidance application in operation 709. In operation 710, the user device may compare the guidance application with the sensor information to analyze exercise movements. Here, the user device may provide the guidance application corresponding to a current state of the user. The user device may compare sensor information by a sensor on the user moving based on the provided guidance application with sensor information of the guidance application. The user device may determine whether movements of the user and a timing of the movements correspond to those of an exercise program provided by the guidance application and provide a determination result to the user in operation 711.

The user device may analyze movement patterns and calorie consumption of the user based on the sensor information using the sensor information sensed by the acceleration sensor or use previously stored movement patterns and calorie consumption of the user. The user device may determine calorie consumption and exercise movements of the user moving according to the guidance application based on the movement patterns and calorie consumption of the user. Here, the user device may determine calorie consumption of the user based on calories determined according to the guidance application.

The user device may verify whether the user progresses appropriately in an exercise according to the guidance application and adjust intensity of the guidance application provided to the user. That is, when the user is not performing an exercise well, the user device may reduce the intensity of the guidance application to provide feedback. When the user is performing the exercise well, the user device may increase the intensity of the guidance application to provide feedback.

When the user device is not in the exercise guidance mode NO in operation 708, the user device may acquire sensor information on acceleration and analyze movement patterns and calorie consumption of the user according to the sensor information in operation 713. Here, the user device may also analyze the movement patterns and calorie consumption of the user in the exercise guidance mode.

The user device may store the analyzed movement patterns and calorie consumption in operation 714. Here, the stored movement patterns and calorie consumption may be used as information for comparing with exercise movements and calorie consumption of the user moving according to the guidance application.

Figure 8:
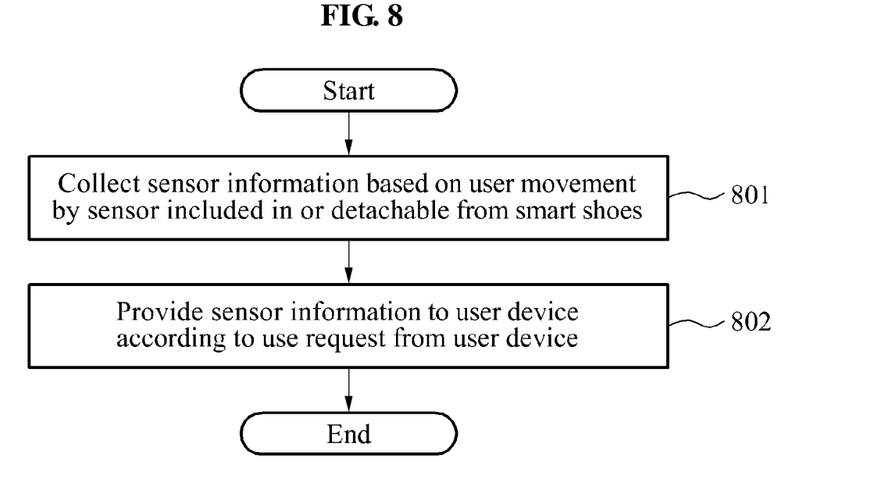
FIG. 8 is a flowchart illustrating an operating method of smart shoes according to an embodiment.

FIG. 8 is a flowchart illustrating an operating method of smart shoes according to an embodiment.

In operation 801, the smart shoes may include at least one of a pressure sensor to sense pressure in the smart shoes, a temperature sensor to sense temperature in the shoes, an acceleration sensor to sense a movement of the shoes and an altitude sensor to sense altitude. The acceleration sensor may be a triaxial acceleration sensor to detect a movement of a user wearing the smart shoes. Here, the sensors may operate as separate modules detachable from the shoes.

The smart shoes may collect sensor information output from at least one of the pressure sensor, the temperature sensor, the acceleration sensor and the altitude sensor.

In operation 802, the smart shoes may provide the collected sensor information to a user device according to a request from the user device.

Figure 9:
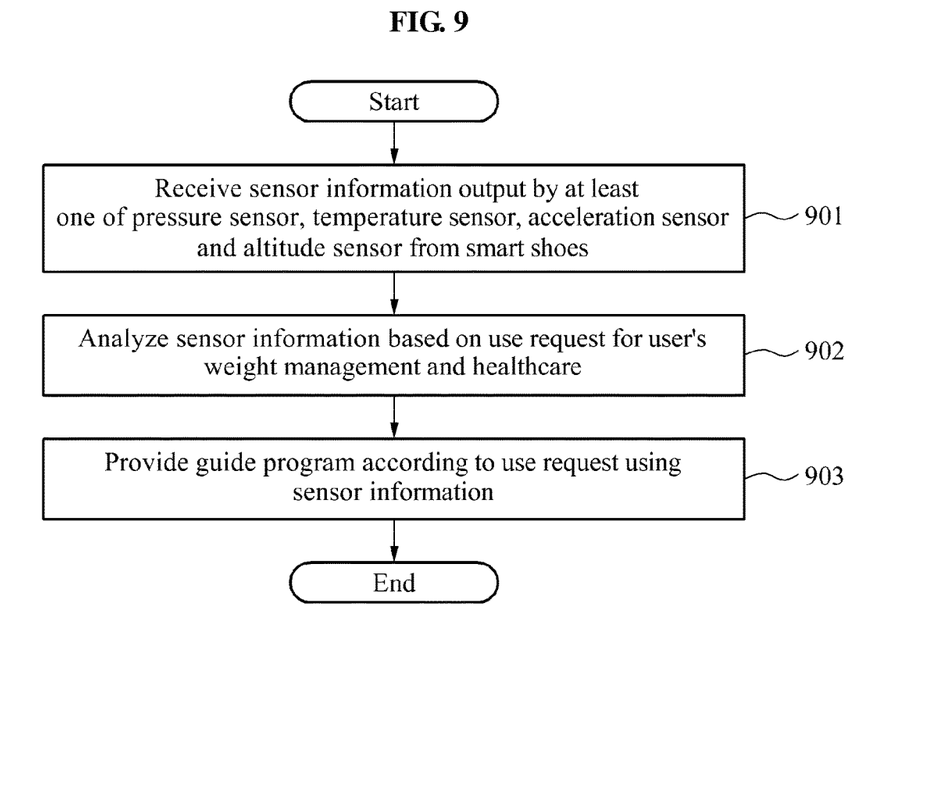
FIG. 9 is a flowchart illustrating an operating method of a user device according to an embodiment.

FIG. 9 is a flowchart illustrating an operating method of a user device according to an embodiment.

In operation 901, the user device may receive, from smart shoes, sensor information output from at least one of a pressure sensor, a temperature sensor, an acceleration sensor and an altitude sensor.

In operation 902, the user device may analyze the sensor information for weight management and healthcare for a user according to a request. In detail, the user device may analyze weight of the user based on a weight estimating algorithm for measuring a weight of the clothes worn by the user. Here, the weight estimating algorithm may measure the weight of the clothes based on sensor information sensed by the temperature sensor. Here, measured temperature may be recorded as data related to the weight of the user, to be used for determining accuracy of a weight.

The user device may analyze physical balance for healthcare for the user based on a foot pressure distribution analysis algorithm using foot pressure distribution according to the weight of the user. When measuring foot pressure distribution, the user device may also record a possibility associated with a direction in which the user carries a bag or object for use in determining an accuracy of a weight. Further, the user device may also record a temperature and a direction in which the user carries a bag or object, thereby minimizing noise when data recorded over a long period of time is used.

In operation 903, the user device may analyze, for user healthcare, at least one of an exercise type, an exercising style, an exercise duration, and an exercise intensity according to a user movement using the sensor information. The user device may analyze at least one of activity patterns and calorie consumption according to a user movement. Further, the user device may help the user to properly follow exercise using a guidance application included in the user device. Here, the user device may provide feedback on whether the user performs motions properly when compared to motions of the guidance application. The user device may output an analysis result of the sensor information.

The foregoing methods according to the exemplary embodiments of the present invention may be recorded in non-transitory computer-readable media including program instructions to implement various operations embodied by a computer. The media may also include, alone or in combination with the program instructions, data files, data structures, and the like. The program instructions recorded in the media may be designed and configured specially for the present invention or be known and available to those skilled in computer software.

Although a few exemplary embodiments of the present invention have been shown and described, the present invention is not limited to the described exemplary embodiments. Instead, it would be appreciated by those skilled in the art that various changes and modifications may be made to these exemplary embodiments without departing from the principles and spirit of the invention. Therefore, the scope of the present invention is not limited to the foregoing exemplary embodiments but is defined by the claims and their equivalents.

What is claimed is:

1. A smart shoe system comprising:
a smart shoe and a user device;
wherein the smart shoe comprises:
a computing device comprising at least one processor to collect sensor information, using a detachable sensor in the smart shoe, based on movement of a user; and
a communication circuit to provide the collected sensor information to the user device according to a request from the user device,
wherein the sensor comprises a pressure sensor, a temperature sensor to sense a temperature in the smart shoe, an acceleration sensor to sense a movement of the smart shoe, and an altitude sensor to sense an altitude,
wherein a volume of an insole or an inside bottom portion of the smart shoe is configured to be adjusted in accordance with a size and shape of a foot joint, measured based on as measured by the pressure sensor applied to the insole or inside bottom portion of the smart shoe a pressure,
wherein the user device, comprising at least one processor, analyzes a foot pressure distribution of the user, analyzes a weight of the user based on a volume of clothes according to the temperature in the smart shoe, and provides a guidance program according to the foot pressure distribution and the weight of the user,
wherein the user device, in order to determine a change in a walking manner of the user, is configured to receive an input of initial weight information on the user from the pressure sensor for measuring the foot pressure distribution of the user, to measure a new foot pressure distribution of the user in a stationary state detected by the acceleration sensor included in the smart shoe, to compare the foot pressure distribution, measured based on the input, with the new foot pressure distribution, to present a comparison result, including information on whether levels of the foot pressure distribution, measured based on the input, and the new foot pressure distribution, are higher or lower than predetermined levels, and to identify the change in the walking manner of the user based on the comparison result.

2. The smart shoe of claim 1, wherein the pressure sensor is disposed on at least one of the inside bottom portion of the smart shoe and an instep contact surface coming in contact with an instep of a foot of the user to measure the weight of the user based on the size and shape of the foot joint of the user.

3. A user device comprising:
a communication circuit to receive, from a smart shoe, sensor information output by a pressure sensor, a temperature sensor, an acceleration sensor and an altitude sensor;
a computing device comprising at least one processor to analyze a foot pressure distribution of a user and to analyze a weight of the user based on a volume of clothes according to a temperature in the smart shoe and to provide a guidance program using the analyzed foot pressure distribution and the analyzed weight of the user, and
wherein the computing device, in order to determine a change in a walking manner of the user, is configured to receive an input of initial weight information on the user from the pressure sensor for measuring the foot pressure distribution of the user, to measure a new foot pressure distribution of the user in a stationary state detected by the acceleration sensor included in the smart shoe, to compare the foot pressure distribution, measured based on the input, with the new foot pressure distribution, to present a comparison result, including information on whether levels of the foot pressure distribution, measured based on the input, and the new foot pressure distribution, are higher or lower than predetermined levels, and to identify the change in the walking manner of the user based on the comparison result.

4. The user device of claim 3, wherein the computing device analyzes the weight of the user based on a weight change of the user, based on a change in the volume of clothes worn by the user with a change in temperature, when measuring the weight.

5. The user device of claim 3, wherein the computing device analyzes the foot pressure distribution according to the weight of the user based on the sensor information output by the pressure sensor.

6. The user device of claim 3, wherein the computing device analyzes at least one of an activity pattern and calorie consumption based on a movement of the user, the movement sensed by the acceleration sensor.

7. The user device of claim 3, wherein the computing device provides the guidance program comprising at least one of an exercise type, an exercising style, an exercise duration, and an exercise intensity based on a movement of the user, the movement sensed by the acceleration sensor.

8. The user device of claim 3, wherein the computing device compares whether the sensor information corresponds to a new sensor information, measured through the guidance program, and provides a result of the comparison of the sensor information to the user.

9. The user device of claim 8, wherein the computing device shares the result of the comparison of the sensor information, using a network connecting different users.

10. A method of providing sensor information to smart shoe, the method comprising:
wherein the smart shoe include a computing device, the computing device comprising at least one processor, and a communication circuit,
collecting, by computing device, sensor information based on a user movement using a detachable sensor in the smart shoe; and
providing, by the communication circuit, the collected sensor information to a user device according to a request from the user device,
wherein the sensor comprises a pressure sensor to sense pressure in the smart shoe, a temperature sensor to sense temperature in the smart shoe, an acceleration sensor to sense a movement of the smart shoe, and an altitude sensor to sense an altitude, and
wherein a volume of an insole or an inside bottom portion of the smart shoe is adjusted in accordance with a size and shape of a foot joint, measured based on the pressure applied to the insole or inside bottom portion of the smart shoe,
wherein the user device processes below steps (1) to (3) using at least one processor,
(1) analyzing a foot pressure distribution of the user,
(2) analyzing a weight of the user based on a volume of clothes according to the temperature in the smart shoe, (3) providing a guidance program according to the foot pressure distribution and the weight of the user, wherein the computing device determines a change in a walking manner of the user by below steps (1) to (5),
(1) receiving an input of initial weight information on the user from the user for measuring the foot pressure distribution of the user;
(2) measuring a new foot pressure distribution of the user in a stationary state detected by the acceleration sensor included in the smart shoe;
(3) comparing the foot pressure distribution, measured based on the input, with the new foot pressure distribution;
(4) presenting a comparison result including information on whether levels of the foot pressure distribution measured based on the input and the new foot pressure distribution are higher or lower than predetermined levels; and
(5) identifying the change in the walking manner of the user based on the comparison result.

11. The method of claim 10, wherein the pressure sensor is disposed on at least one of the inside bottom portion of the shoe and an instep contact surface coming in contact with an instep of a foot of the user to measure the weight of the user based on a distribution of foot joints of the user.

12. A method of providing a guidance program to a user device, the method comprising:
wherein the user device includes a communication circuit and a computing device, the computing device comprising at least one processor,
receiving, by the communication circuit, from a smart shoe, sensor information output by a pressure sensor, a temperature sensor, an acceleration sensor, and an altitude sensor;
analyzing, by the computing device, a foot pressure distribution of a user and analyzing, by the computing device, a weight of the user based on a volume of clothes according to a temperature in the smart shoe; and
providing, by the computing device, a guidance program according to the analyzed foot pressure distribution and the analyzed weight of the user, and
wherein the computing device determines a change in a walking manner of the user by below steps (1) to (5),
(1) receiving an input of initial weight information on the user from the pressure sensor for measuring the foot pressure distribution of the user;
(2) measuring a new foot pressure distribution of the user in a stationary state detected by the acceleration sensor included in the smart shoe;
(3) comparing the foot pressure distribution, measured based on the input, with the new foot pressure distribution;
(4) presenting a comparison result including information on whether levels of the foot pressure distribution measured based on the input and the new foot pressure distribution are higher or lower than predetermined levels; and
(5) identifying the change in the walking manner of the user based on the comparison result.

13. The method of claim 12, wherein the analyzing comprises analyzing the weight of the user based on a weight change of the user.

14. The user device of claim 12, wherein the computing device analyzes the weight of the user based on a weight change of the user, based on a change in the volume of clothes worn by the user with a change in temperature.

15. The method of claim 12, wherein the analyzing analyzes at least one of an activity pattern and calorie consumption based on a movement of the user, the movement sensed by the acceleration sensor.

16. The method of claim 12, wherein the providing provides the guidance program comprising at least one of an exercise type, an exercising style, an exercise duration, and an exercise intensity based on a movement of the user, the movement sensed by the acceleration sensor.

17. The method of claim 12, wherein the providing compares whether the sensor information corresponds to a new sensor information, measured through the guidance program, and provides a result of the comparison of the sensor information to the user.

18. The method of claim 17, further comprising sharing, by the computing device, the result of the comparison of the sensor information, using a network connecting different users.

* * * * *